United States Patent [19]

La Force

[11] Patent Number: 5,271,275
[45] Date of Patent: Dec. 21, 1993

[54] METHOD AND APPARATUS FOR TESTING WIRE

[76] Inventor: Jeffrey La Force, P.O. Box 3616, Napa, Calif. 94558

[21] Appl. No.: 788,505

[22] Filed: Nov. 6, 1991

[51] Int. Cl.$^5$ .................. G01N 29/24; G01N 29/26
[52] U.S. Cl. ........................... 73/622; 73/629; 73/597
[58] Field of Search ............... 73/622, 620, 629, 638, 73/639, 597

[56] References Cited

U.S. PATENT DOCUMENTS

| | | | |
|---|---|---|---|
| 3,612,920 | 10/1971 | Bantz | 73/639 |
| 4,302,976 | 12/1981 | Ball | 73/639 |
| 4,722,225 | 2/1988 | Hardy et al. | 73/622 |
| 4,856,334 | 8/1989 | Shearer et al. | 73/639 |
| 4,995,320 | 2/1991 | Sato et al. | 73/638 |

*Primary Examiner*—Tom Noland
*Assistant Examiner*—Rose M. Finley
*Attorney, Agent, or Firm*—Richard C. Litman

[57] ABSTRACT

A method and apparatus for testing wire and, more specifically, testing the wire thickness and the wire roll of a trolley wire. The apparatus includes a jig assembly connected to a data acquisition system carried by a mobile unit. The jig assembly includes a transducer probe which transmits and receives an ultrasonic signal and an encoder which provides a pulse train corresponding to distance traveled. The ultrasonic signal is transmitted into the trolley wire and a reflected wave is received. The data acquisition system includes an ultrasonic scope, an analog to digital converter, a central processing unit, and a divider circuit. The ultrasonic scope provides a time analog signal based on the time of flight comparison between the transmitted ultrasonic signal and the reflected wave. The time analog signal is converted to a digital signal through an analog to digital converter. A trigger pulse is provided by a divider circuit based on a predetermined number of pulses from the encoder. In response to the trigger pulse, the digital signal is processed by the central processing unit to provide a corresponding wire thickness of the trolley wire. If the trolley wire is twisted, the reflected wave will be lost and the central processing unit will void the sample. The central processing unit compiles, organizes, summarizes, and stores the data in a useful form. A couplant fluid, for example, water, is supplied continuously to the surface of the segment of the trolley wire under test via a water reservoir within the transducer probe subassembly.

18 Claims, 6 Drawing Sheets

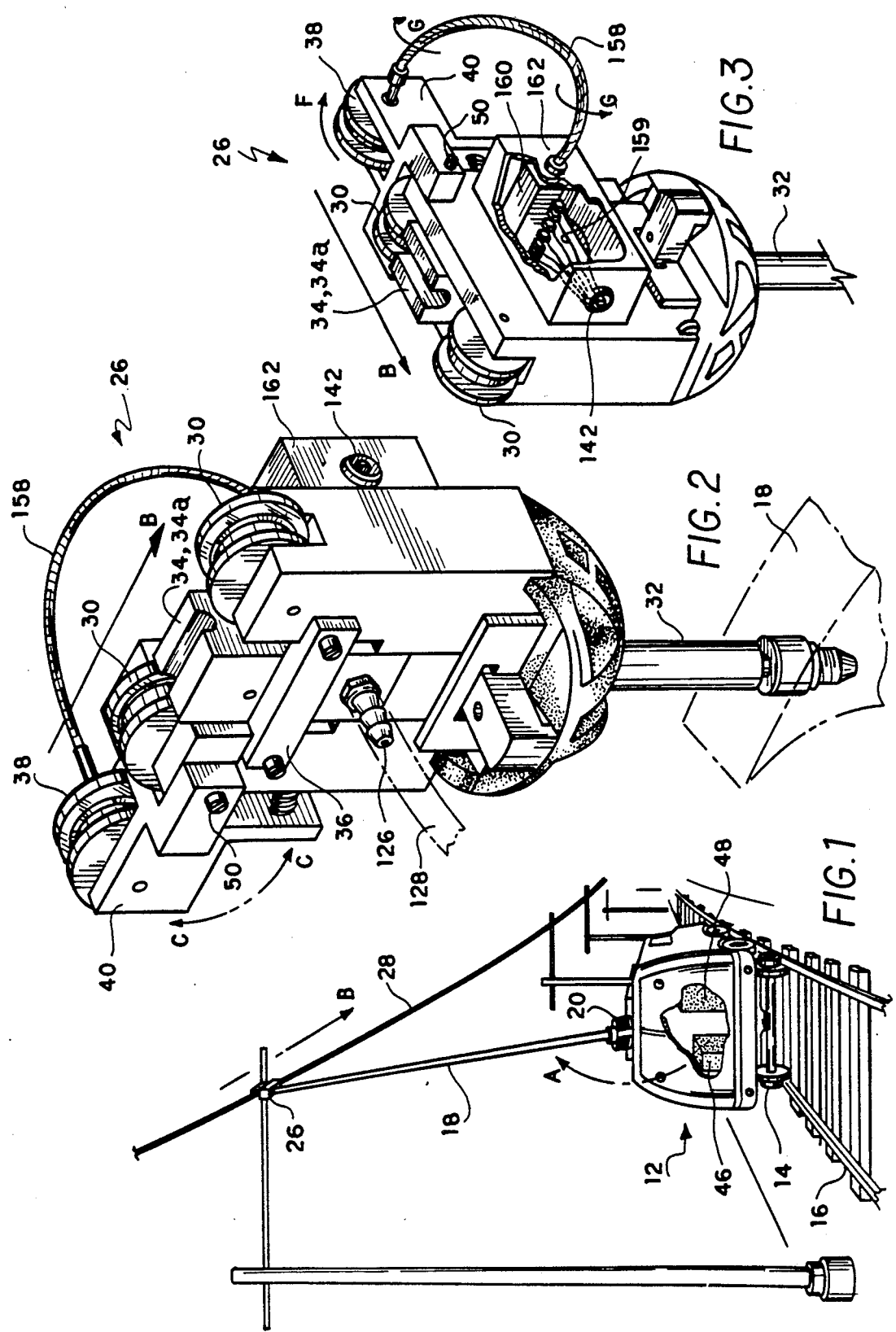

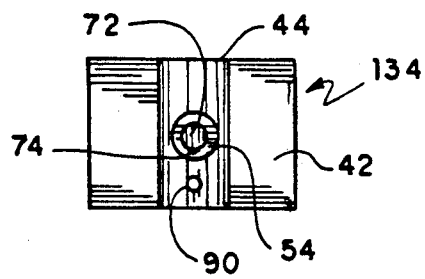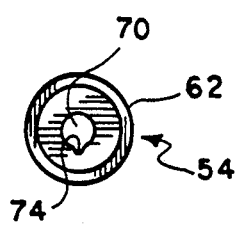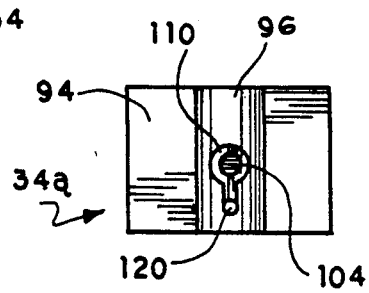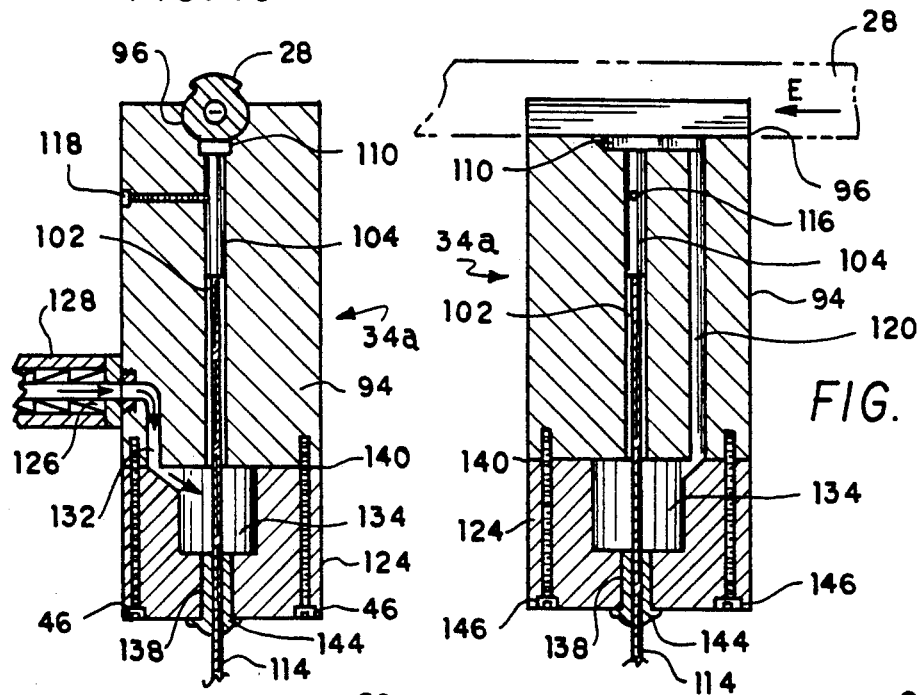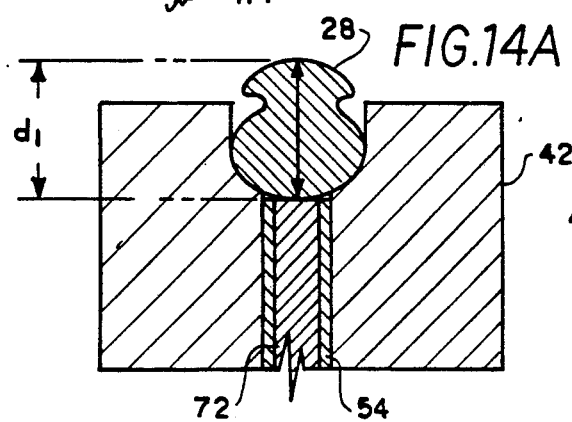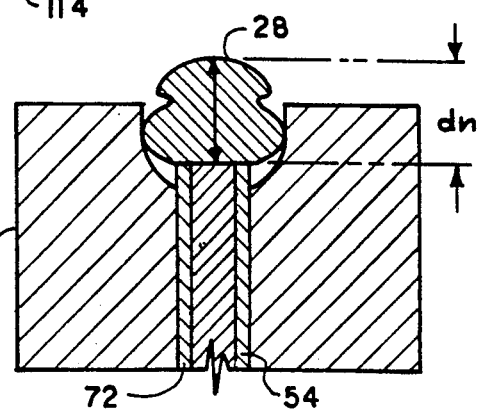

TRANSMITTED WAVE

REFLECTED WAVE

TRANSMITTED WAVE

REFLECTED WAVE

METHOD AND APPARATUS FOR TESTING WIRE

BACKGROUND OF THE INVENTION

1. Field of the Invention

The present invention relates to a method and apparatus for testing wire, that is for measuring deviations in wire and more particularly, for measuring deviations in the wire thickness and wire roll of trolley wire.

2. Description of Prior Art

Trolley wires have to be tested periodically in a effort to disclose areas subject to failure. One type of test includes testing the wear of the trolley wire, that is testing the trolley wire for a minimum wire thickness. The results of the test prompt the replacement of the trolley wire prior to failure and establishes a wire wear pattern which is useful in projecting a budget for the future replacement of the trolley wire. Trolley wires are also tested upon the completion of their installation to determine if the installation has been conducted in compliance with the contract specifications which require that the trolley wire not have any roll or twist. A roll or twist in the trolley wire will cause premature wear of the trolley wire.

Trolley wires are currently tested using unsophisticated methods. One method currently in use involves the visual inspection of the trolley wire. This is accomplished through individuals who walk along the right of way beneath the trolley wire visually inspecting the trolley wire from the ground surface for obvious wear or damage. Since the height of the trolley wire ranges from fourteen feet to twenty-four feet, this type of inspection offers very limited results. Another method requires a physical inspection of the trolley wire with the use of micrometers or calipers. This method is very time consuming and laborious. Moreover, there are areas of limited access. One such area where access is limited is adjacent the hanger where a rigid segment of trolley wire exists. This is an area of accelerated wear. A more accurate and efficient method and apparatus would prove to be of greater value then the methods currently in use.

U.S. Pat. No. 4,586,379 issued may 6, 1986 to Frederick R. Burkhardt, Jr. discloses a remote controlled ultrasonic transducer assembly which includes a platform movable along an arm projecting from a carriage on a track around a pipe. The assembly includes a pipe contacting surface which lies close to the pipe and a universal joint which is maneuvered to cause the assembly to move circumferentially around the pipe, pressing the assembly against the pipe and moving along the weld controlling the angle of the transducer relative to the direction of the movement. A couplant fluid is continuously supplied to the pipe surface under test to couple the pipe surface and the ultrasonic transducer assembly. U.S. Pat. No. 4,523,468 issued Jun. 18, 1985 to Thomas Derkacs et al. discloses a system including an array of ultrasonic transducers which transmit circumferentially around a cylindrical object and a set of ultrasonic transducers which transmit axially around a cylindrical object. A trigger pulse triggers a single transducer of each set separately while the other transducers operate in a receiving mode to receive a reflected wave. A central processor unit uses a measurement of the time of flight relationship of the ultrasonic signal traveling from the transmitting transducer to the defect and from the defect to the receiving transducer to triangulate the location of the reflective defect. U.S. Pat. No. 4,375,165 issued Mar. 1, 1983 to Arie de Sterke discloses an assembly which circumferentially inspects the welded joints in a pipeline. A set of ultrasonic probes direct ultrasonic waves into and receive ultrasonic waves from the interior surface of the pipe in order to measure the pipe diameter, the wall thickness, and inspect the welded joint. The system is a mobile system which includes a multicrystal switch controlled by a multichannel ultrasonic device for transmitting ultrasonic waves into the pipe material.

SUMMARY OF THE INVENTION

By the present invention, a method and apparatus for testing wire, and more particularly, for measuring deviations in the wire thickness and the wire roll of a trolley wire are provided. The wire testing device comprises a jig assembly which is suspended by a trolley pole which in turn is mounted to a vehicle adapted to support the apparatus. The trolley pole is spring biased so the jig assembly substantially maintains contact with the bottom surface of the trolley wire. The jig assembly contains a set of guide wheels which guide the jig assembly lengthwise along the bottom surface of the trolley wire, a transducer which transmits an ultrasonic signal into the horizontal axis of the trolley wire and senses a reflection of the ultrasonic signal, a roto-pulser or encoder which produces a pulse train which corresponds to the distance the jig assembly moves along the trolley wire, and a data acquisition system which acquires, compiles, organizes, summarizes and stores the data. The data acquisition system includes a central processing unit (CPU), an ultrasonic scope, an analog to digital converter (A to D converter), a divider circuit, and a memory. The CPU continuously processes the pulse train produced by the encoder. Based on a predetermined number of pulses from the encoder, the divider circuit triggers a sample signal and is reset by the CPU. A time analog signal in response to the reflection of the ultrasonic signal is processed in response to the trigger. The time analog signal is produced by the ultrasonic scope based on a time of flight comparison between the transmitted ultrasonic signal and the reflection of the ultrasonic signal. The time analog signal is converted from an analog signal to a digital signal by the A to D converter. The CPU processes, compiles, organizes and summarizes the data in a useful form and stores the data on a storage medium.

Accordingly, one object of the present invention is provide an accurate method and apparatus for sampling deviations in the wire thickness and the wire roll of trolley wires and to provide a true location pinpointing where the deviations exists.

Another object of the present invention is to provide a time efficient method and apparatus for testing trolley wire which will produce a greater sample rate.

Another object of the present invention is to provide a method and apparatus for testing trolley wire which compiles and organizes the data into a useful form.

Further, an object of the present invention is to provide a method and apparatus for testing trolley wire which requires fewer man hours then methods presently used.

These and other objects of the present invention will become readily apparent upon further review of the following specification and drawings.

BRIEF DESCRIPTION OF THE DRAWINGS

FIG. 1 is an environmental view according to the apparatus of the present invention as it appears supported by a vehicle adapted to support it.

FIG. 2 is a perspective view showing the jig assembly according to the apparatus of the present invention.

FIG. 3 is a perspective view of the jig assembly according to the apparatus of the present invention showing a partial cutaway of the encoder housing.

FIG. 8 is a top plan view of the transducer probe subassembly of the preferred embodiment according to the apparatus of the present invention.

FIG. 9 is a top view plan of the plunger of the preferred embodiment according to the apparatus of the present invention showing the vertical keyway machined along the inside forward surface of the axial cylindrical bore.

FIG. 10 is a cross-sectional elevational view of the transducer probe subassembly of a first alternative embodiment according to the apparatus of the present invention.

FIG. 11 is a cross-sectional elevational view of the transducer probe subassembly of the first alternative embodiment according to the apparatus of the present invention.

FIG. 12 is a top plan view of the transducer probe subassembly of the first alternative embodiment according to the apparatus of the present invention.

FIG. 14A is a cross-sectional view of the trolley wire under test illustrating a segment where deviation in the wire thickness of the trolley wire is not present.

FIG. 14B is a cross-sectional view of the trolley wire under test illustrating a segment where deviation in the wire thickness of the trolley wire exists due to wire wear.

Similar reference characters denote corresponding features consistently throughout the attached drawings.

DETAILED DESCRIPTION OF THE PREFERRED EMBODIMENTS

Figure 4:
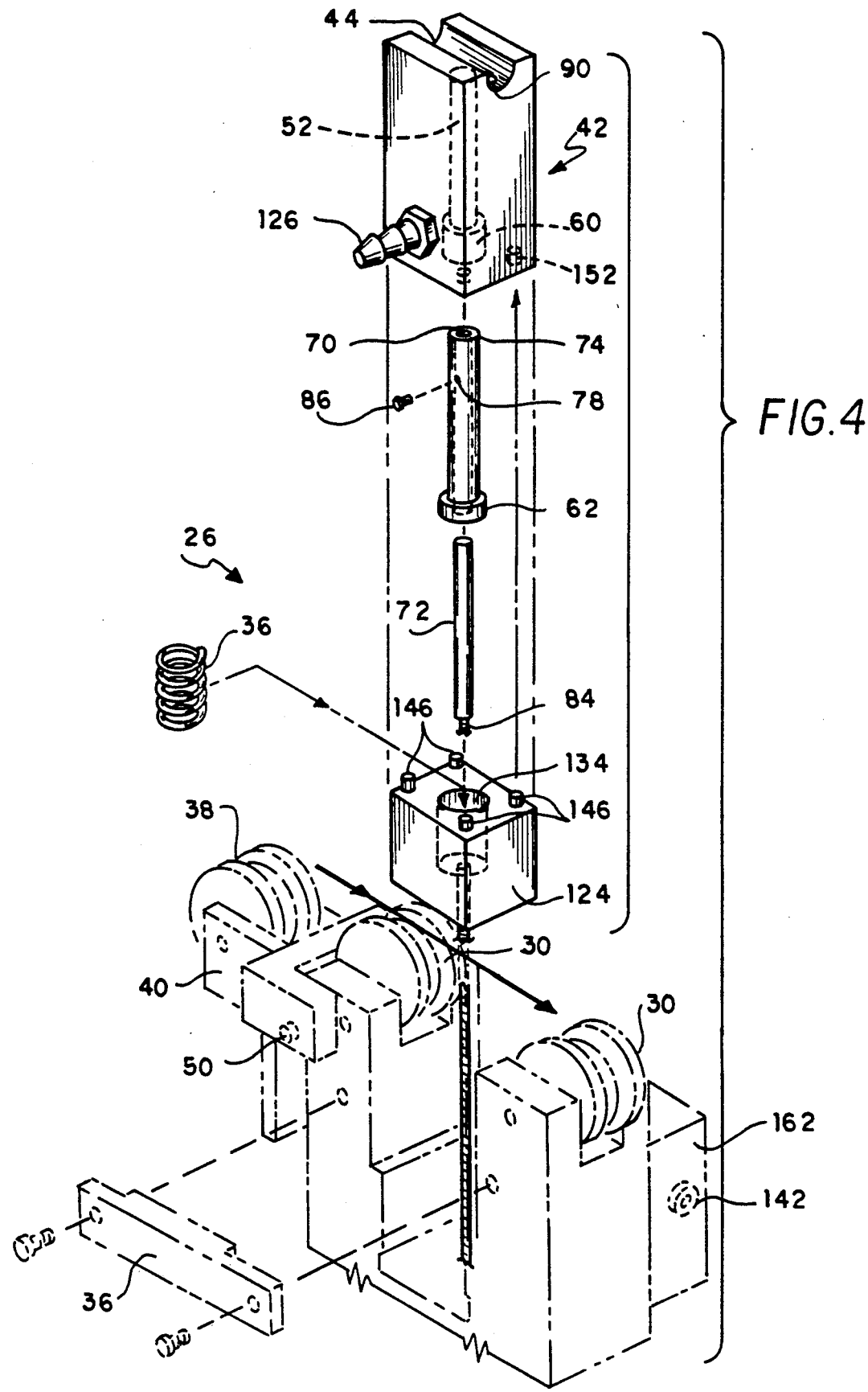
FIG. 4 is a partially exploded perspective view of the jig assembly and the transducer probe subassembly according to the apparatus of the preferred embodiment of the present invention.

Now, referring to the drawing, more particularly FIG. 1, which shows a vehicle 12 adapted to support the apparatus. The vehicle 12 is modified with a set of rail wheels 14 which enable it to follow a course of track 16. An extension 32 extending from the bottom of the jig assembly 26 is attached to a boom or trolley pole 18 which is secured to a spring loaded base 20 which is mounted to the top surface of the vehicle 12 adjacent the rear of the vehicle 12. The trolley pole 18 is spring biased in the direction A to keep the jig assembly 26 in constant contact with the trolley wire 28. The vehicle 12 houses a water storage tank and a pump 46 which supplies water to a water reservoir contained within the transducer probe subassembly 34,34a (shown in FIG. 6, FIG. 7, FIG. 10, and FIG. 11). The water serves as a couplant fluid between a transducer probe 72 and the trolley wire 28 under test. In addition, the vehicle 12 possesses a power supply 48 which provides power for the operation of data acquisition system 10 (shown in FIG. 13).

Figure 5:
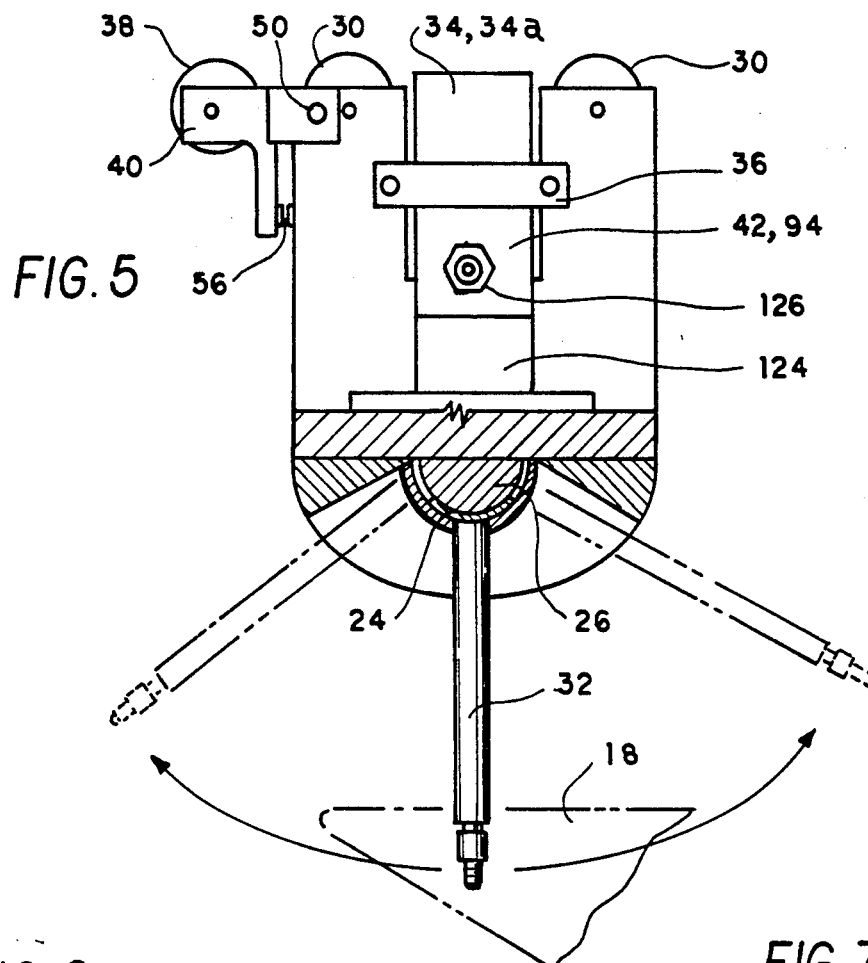
FIG. 5 is a side elevational view of the jig assembly according to the apparatus of the present invention showing a cross-section of the ball and socket configuration.
Figure 6:
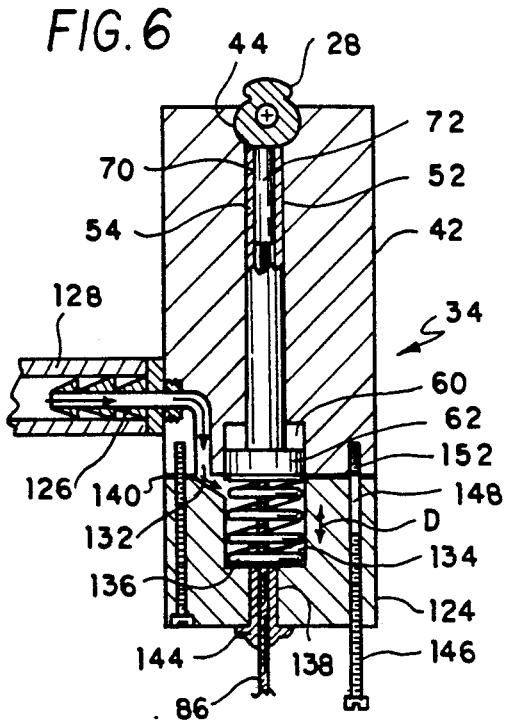
FIG. 6 is a cross-sectional elevational view of the transducer probe subassembly of the preferred embodiment according to the apparatus of the present invention.
Figure 7:
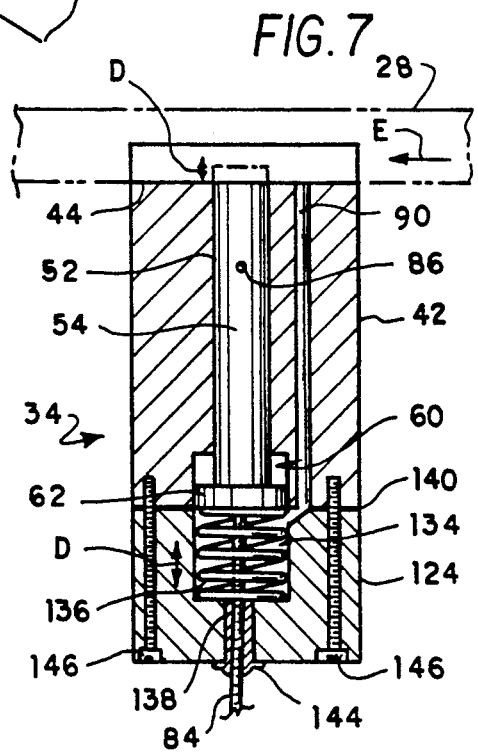
FIG. 7 is a cross-sectional elevational view of the transducer probe subassembly of the preferred embodiment according to the apparatus of the present invention.

Referring also to FIG. 2, FIG. 3, and FIG. 4, the jig assembly 26 moves in the direction B along the length of the trolley wire 28 being tested. A set of guide wheels 30 makes contact with the bottom surface of the trolley wire 28. This contact is guaranteed to be continuous by the spring bias of the trolley pole 18 in the direction A. A transducer probe subassembly 34,34a is retained in the jig assembly 26 between the set of guide wheels 30 by a clamping means 36. This transducer probe subassembly 34,34a is arranged in the jig assembly 26 to maintain contact with the bottom surface of the trolley wire 18. A roto-pulser wheel 38 is axially mounted on a spring biased pivoting member 40. The pivoting member 40 includes a pivot point 50 and a spring 56. The pivoting member 40 is spring biased in the direction C keeping the roto-pulser wheel 38 in contact with the bottom surface of the trolley wire 28. A ball 22 and socket 24 configuration (shown in FIG. 5) allows the entire jig assembly 26 to pivot on the trolley pole 18 while the vehicle 12 is in motion, thus ensuring the guide wheels 30, the transducer probe subassembly 34,34a, and the roto-pulser wheel 38 stay in contact with the bottom surface of the trolley wire 28.

FIG. 4, FIG. 6, FIG. 7, FIG. 8 and FIG. 9 show the transducer probe subassembly of 34 the preferred embodiment. This transducer probe subassembly 34 is used in conjunction with the trolley wire wear or wire thickness test. The transducer probe subassembly 34 includes a rectangular upper body 42 which has a semi-circular raceway 44 adjacent the top horizontally extending from the front to the rear of the upper body 42. A vertical bore 52 is centrally located within the upper body 42 to accommodate a plunger 54 which is inserted through the bottom of the upper body 42. A lower portion of the upper body 42 has a slightly larger diameter bore 60 to accommodate a flange 62 on the lower portion of the plunger 54. This slightly larger diameter bore 60 within the lower portion of the upper body 42 offers a restricted axial movement D of the plunger 54. The plunger 54 is substantially the same length as the upper body 42 and has two separate diameters which are integrally joined together in a stepwise manner. The upper portion of the plunger 54 includes an outside diameter that is machined within a close tolerance of the vertical bore 52 within the upper portion of the upper body 42. The lower portion of the plunger 54 includes a flange 62 which has a slightly greater diameter than the upper portion. The plunger 54 includes an axial cylindrical bore 70. The transducer probe 72 is a cylindrical body having an outside diameter which is within a close tolerance of the diameter of the axial cylindrical bore 70 within the plunger 54. A vertical keyway 74 is cut along the inside forward surface of the axial cylindrical bore 70 of the plunger 54 extending from the top surface to the bottom. This keyway 74 permits the flow of water from the lower portion of the plunger 54 to the top surface of the plunger 54. The transducer probe 72 is inserted into the bottom of the axial cylindrical bore 70 of the plunger 54 until the top surface of the transducer probe 72 is adjacent the top of the plunger 54. The transducer probe 72 is secured within the plunger 54 by a set screw 86 tightened into the threaded hole 78. The top of the plunger 54 just slightly exceeds the top surface of the transducer probe 72 to provide protection for the transducer probe 72 against wear. The transducer probe conductors 84 extends from the bottom of the plunger 54. With the plunger 54 in place within the upper body 42, the axial movement D (see FIG. 6 and FIG. 7) enables the plunger 54 to slightly exceed the lower surface of the semi-circular raceway 44. The plunger 54 and the transducer probe subassembly 34 are both fabricated of a material which offers a high resistance to wear. A conduit or a prewash port 90 is also provided through the upper body 42 which surfaces forward the plunger 54. This prewash port 90 provides for the flow of water from the lower portion to the upper portion of the upper body 42. The water is carried in the direction E by the static force of the trolley wire 28. This water delivery combination provides a continuous couplant between the transducer probe 72 and the trolley wire 28 being tested.

FIG. 10, FIG. 11, and FIG. 12 show the transducer probe subassembly 34a of a first alternative embodiment. This transducer probe subassembly 34a is used in conjunction with the trolley wire roll test. The transducer probe subassembly 34a is comprised of a rectangular upper body 94 with a semi-circular raceway 96 in the top horizontally extending from the front to the rear of the upper body 94. A vertical cylindrical bore 102 is centrally bored within the upper body 94 to accommodate a transducer probe 104. The vertical cylindrical bore 102 begins at the bottom surface of the upper body 94 and extends through the semi-circular raceway 96 and penetrating the top surface of the upper body 94. The upper body 94 includes a deformed circular recess 110 centralized in the lower surface of the semi-circular raceway 96. The transducer probe 104 has an outside diameter within a close tolerance of the diameter of the vertical cylindrical bore 102. The transducer probe 104 is inserted into the vertical cylindrical bore 102 through the bottom surface of the upper body 94 with the transducer probe conductors 114 extending downward out of the vertical cylindrical bore 102. The top surface of the transducer probe 104 when inserted in the vertical cylindrical bore 102 is flush with the bottom surface of the deformed circular recess 110 to prevent the transducer probe 104 from making contact with the trolley wire 28, thus protecting the transducer probe 104. The upper body 94 is fabricated from a material which offers a high resistance to wear. The transducer probe 104 is affixed within the vertical cylindrical bore 102 adjacent the top surface of the semi-circular raceway by a set screw 118 tightened into a threaded hole 118. A conduit or water delivery port 120 extends from the bottom surface of the upper body 94 through the top surface. This water delivery port 120 extends through the top surface of the upper body 94 within the confines of the deformed circular recess 110 forward the transducer probe 104. The water is supplied through the water delivery port 120 from the bottom surface of the upper body 94. The deformed circular recess 110 functions as a water dam to maintain a constant couplant fluid between the transducer probe 104 and the trolley wire 28. The water is carried in the direction E by the static force of the trolley wire 28.

Referring to FIG. 4, FIG. 6, FIG. 7, FIG. 8, FIG. 9, FIG. 10, FIG. 11, and FIG. 12, the transducer probe subassembly 34,34a also includes a substantially square base 124 in both the preferred and the alternative embodiments. The base 124 functions as part of the water delivery system. An inlet port 126 which is connected to the water supply line 128 is located on the side of the upper body 42,94. The water supply is stored in a storage container 46 in the vehicle 12 adapted (see FIG. 1) to support the apparatus. The water is pumped from the vehicle 12 to the inlet port 126 located on the upper body 42,94. It is directed downward to the base 124 through a conduit 132 located within the upper body 42,94. The base 124 contains a reservoir 134 and is configured to deliver the water to the vertical keyway 74 and prewasher port 90 or the water delivery port 120 depending on the embodiment. In addition to the base 124 containing a reservoir 134, it supports a spring 136 which axially or vertically biases in the direction D the plunger 54 of the preferred embodiment. The conductors 84,114 from the transducer probe 72,104 are vertically routed through the center of the base 124 (and through the center of the spring 136 in the preferred embodiment) where they exit through a hole 138 in the center of the bottom of the base 124. The top surface of the base 124 is secured to the bottom surface of the upper body 42,94. This is accomplished with four screws 146, each one inserted in a hole 148 located in each of the corners of the base 124. These holes 148 line up with threaded holes 152 in the bottom surface of the upper body 42,94. The four screws 148 are equally torqued to ensure a proper seal between the top surface of the base 124 and the bottom surface of the upper body 42,94. A sealant material, such as a gasket 140, a boot 144, or silicone substance (not shown), is used to seal the area where the base 124 meets the upper body 42,94 and where the conductors 84,114 exits through the bottom of the base 124.

The water is carried in the direction E from the forward end to the rear end of the transducer probe subassembly 34,34a by the static force created by the movement of the jig assembly 26 in the direction B against the trolley wire 28 (shown in FIG. 1). This provides a continuous coupling of the transducer probe 72,104 and the trolley wire 28 under test.

Referring back to FIG. 3, there is shown a Bowden cable 158 leading from the roto-pulser wheel 38 to a roto-pulser or encoder 160 housed in an encoder housing 162 mounted on the side of the jig assembly 26. As the roto-pulser wheel 38 rotates in the direction F by the motion of the jig assembly 26 or the static force of the trolley wire 28, the Bowden cable 158 rotates in the direction G which in turn produces a series of pulses via the encoder 160. The encoder 160 produces 127 pulses per six inch length or segment of trolley wire 28 tested or 100 pulses with each revolution of the roto-pulser wheel 38. Six inches is a common denominator of the specified values permitted within the specifications used within the trolley car industry. The encoder 160 operates on a five volt operating voltage. The operating voltage is supplied to the encoder 160 via a power supply 48 located within the support vehicle 12. The encoder 160 is interfaced with a data acquisition system 10 through a cable (not shown) connected to the connector 142 which is hard wired to the encoder by the conductors 159.

Figure 13:
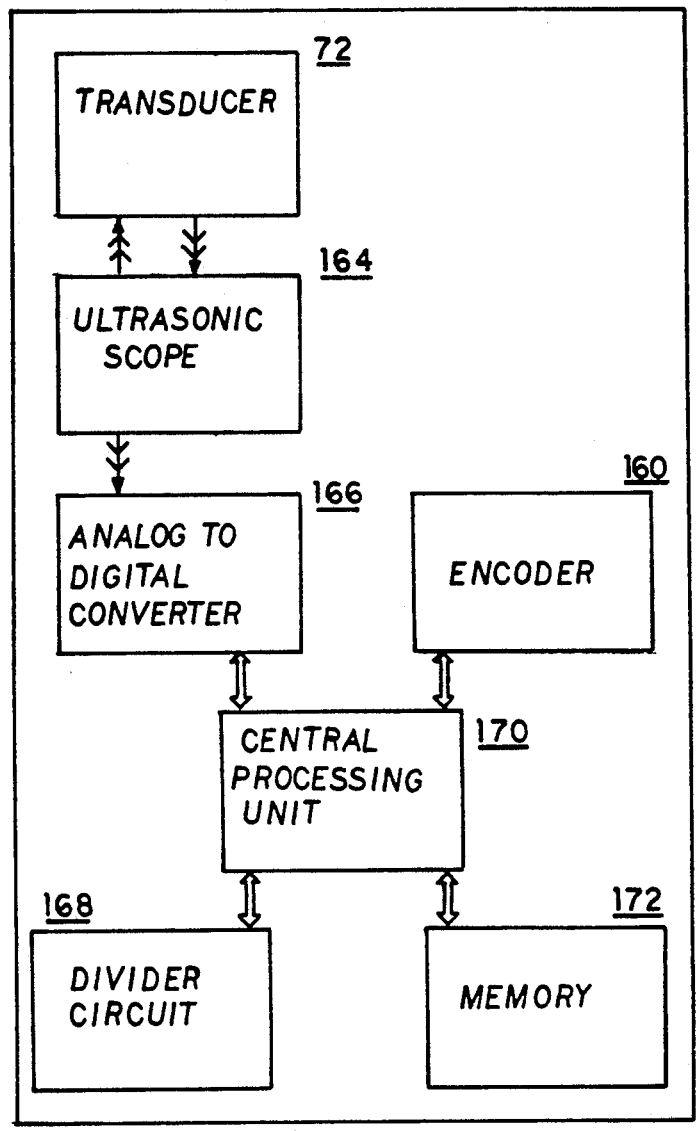
FIG. 13 is a block diagram of the acquisition data system according to the apparatus of the present invention.

FIG. 13 shows a block diagram which comprises a data acquisition system 10 which includes the transducer probe 72, an ultrasonic scope 164, an analog to digital (A to D) converter 166, the encoder 160, a divider circuit 168, a central processing unit (CPU) 170, and a memory 172. The ultrasonic scope 164 produces a time analog signal based on a time of flight comparison between the transmitted ultrasonic signal and the reflection of the ultrasonic signal. The time analog signal is converted to a digital signal by an A to D converter 166. The encoder 160 produces a digital pulse train. This pulse train is transmitted to the CPU 170 and the divider circuit 168. The CPU 170 processes a pulse train continuously. In a predetermined number of pulses, in this case 127 pulses, the divider circuit 168 provides a trigger signal to sample the digital signal from the A to D converter 166. As the trigger signal is produced, the CPU 170 provides a reset signal to the divider circuit 168 which resets the divider circuit 168 to zero whereby the divider circuit 168 begins to count up to the predetermined number of pulses again. The CPU 170 processes the sampled digital signal to provide a four digit code which reflects the actual distance d1, . . . , dn traveled or the wire thickness of the trolley wire 28 (as shown in FIG. 14A and FIG. 14B).

The CPU 170 compiles and organizes the data. The data is sorted to provide a counter and odometer reading, a corresponding wire thickness and deviation, and a running average and ten point average of the wire thickness. In addition, it summarizes the test results. The summary includes the total number of pages, voided samples, rejected samples, accepted samples taken, an ending running average, a deviation average, and a total distance covered.

Figures 15A, 15B:
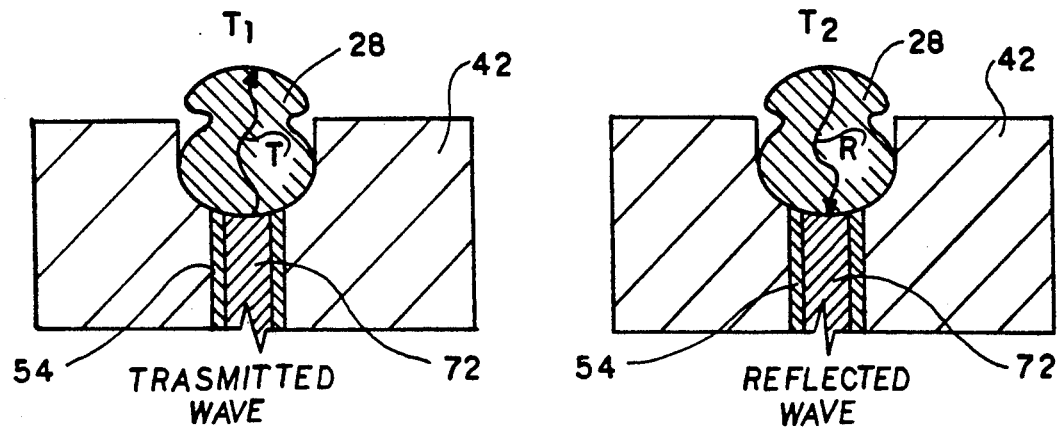
FIG. 15A is a cross-sectional view of the trolley wire under test illustrating the transmission of the transmitted wave at time T1.
FIG. 15B is a cross-sectional view of the trolley wire under test illustrating the reception of the reflected wave at time T2.

Referring to FIG. 15A and FIG. 15B, the method according to the preferred embodiment provides a series of measurements of the wire thickness d1, . . . , dn of the trolley wire 28 utilizing a time of flight relationship. The transducer probe 72 transmits a transmitted wave T through the couplant fluid into the trolley wire 28 at time T1 and senses a reflected wave R at time T2. Since the speed of the ultrasonic wave is constant, the ultrasonic scope uses the travel time (T2−T1) between the transmission of the transmitted wave T and the reflected wave R received to provide a spatial relation which corresponds to the wire thickness d1, . . . , dn of the trolley wire 28. As can be illustrated in FIG. 14a and FIG. 14b, the travel time is greater for a segment of trolley wire 28 with a greater wire thickness d1 and a lesser amount of wear than it is for a segment of trolley wire 28 with a smaller wire thickness dn and greater wear.

Figure 16A:
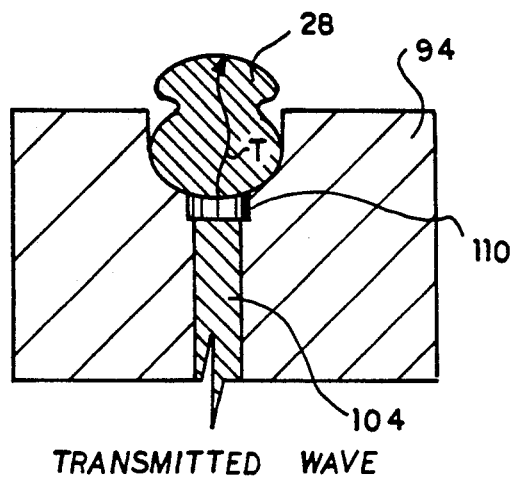
FIG. 16A is a cross-sectional view of the trolley wire illustrating the transmission of the transmitted wave into a segment of trolley wire where wire roll does not exist.
Figure 16B:
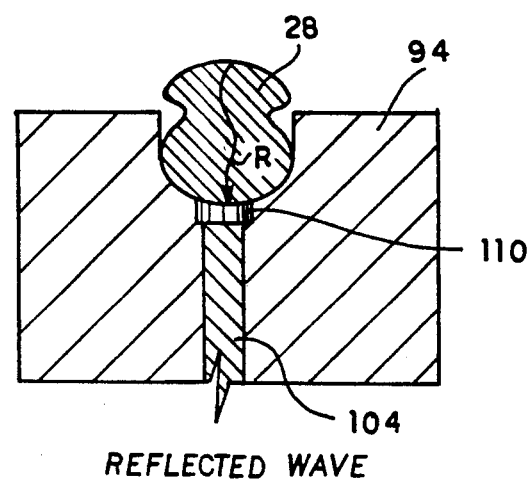
FIG. 16B is a cross-sectional view of the trolley wire illustrating the reception of the reflected wave from a segment of trolley wire where wire roll does not exist.
Figure 17A:
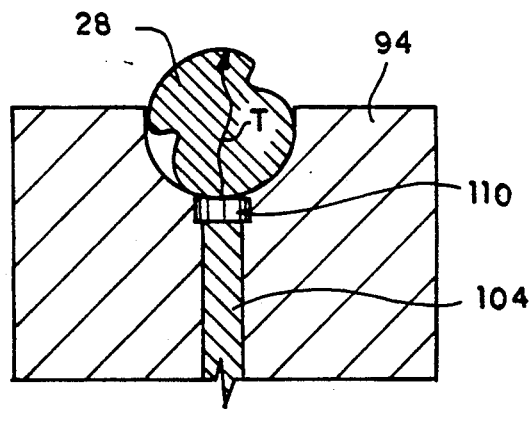
FIG. 17A is a cross-sectional view of the trolley wire illustrating transmission of the transmitted wave into a segment of trolley wire where wire roll is present.
Figure 17B:
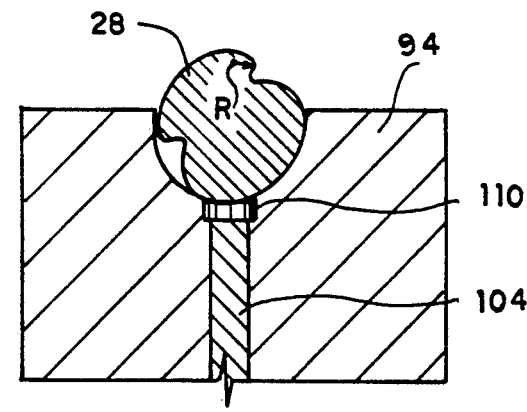
FIG. 17B is a cross-sectional view of the trolley wire illustrating the reception of the reflected wave from a segment of trolley wire where wire roll is present.

Referring to FIG. 16A, FIG. 16B, FIG. 17A, and FIG. 17B, the method according to the alternative embodiment whereby the apparatus indicates wire roll or twist will be discussed. The transducer probe 104 transmits a transmitted wave T into the bottom surface of the trolley wire 28 and awaits a reflected wave R. If the trolley wire 28 is not twisted substantially, a reflected wave will be received as shown in FIG. 16B. If, on the other hand, the trolley wire 28 is twisted substantially, the reflected wave R will be deflected and will not be sensed by the transducer probe 104. Thus, in this test, the apparatus in not sampling deviations but is merely recording reflected waves and a lack of reflected waves would be indicative of a twisted segment of trolley wire 28.

It is to be understood that the present invention is not limited to the embodiments described above, but encompasses any and all embodiments within the scope of the following claims.

I claim:

1. An apparatus for measuring a wire thickness and a roll of a wire having a thickness, said apparatus comprising:

a jig assembly including a transducer probe coupled with the wire and an encoder which controls a sample rate, means to interpose a couplant fluid between said transducer probe and the wire, said transducer probe forming an ultrasonic wave, said ultrasonic wave being transmitted from said transducer probe into the wire, said ultrasonic wave being reflected back from the wire to said transducer probe, and a data acquisition system for measuring and recording a time lapsed between said ultrasonic wave being transmitted and said ultrasonic wave being reflected, whereby wire thickness is derived from said time lapsed and a failure to receive said ultrasonic signal being reflected is indicative of a roll in the wire.

2. The apparatus according to claim 1, wherein said jig assembly includes a means to guide said jig assembly along the wire.

3. The apparatus according to claim 1, where said jig assembly includes a transducer probe subassembly comprising an upper body and a base, said transducer probe, a water reservoir which supplies a continuous couplant fluid through conduit to couple said transducer probe and said wire forming said means to interpose a couplant fluid between said transducer probe and said wire, a water supply inlet port, and a raceway which makes contact with and conforms the configuration of the wire.

4. The apparatus according to claim 3, wherein said upper body includes a plunger and a means defining a centralized vertical bore dimensioned to provide a snug fit relationship with said plunger disposed therein, said plunger being vertically spring biased to ensure said plunger substantially maintains contact with the wire, said plunger including a flange restricting axial movement of said plunger, and a centralized bore which provides a snug fit relationship to accommodate said transducer probe, said transducer probe being disposed within said plunger whereby said transducer probe is recessed within said plunger to provide protection for said transducer probe against making contact with said wire, and a fastening means to secure said transducer probe within said plunger, said plunger further including a keyway which defines a continuous couplant fluid interconnection between said transducer and the wire.

5. The apparatus according to claim 3, wherein said upper body includes a centralized vertical bore having a snug fit relationship to said transducer probe which is disposed therein and a fastening means to secure said transducer probe within said centralized vertical bore, said transducer probe being slightly recessed within said centralized vertical bore whereby said upper body protects said transducer probe from making contact with the wire.

6. The apparatus according to claim 3, wherein a fastening means is provided to secure said upper body to said base to form said water reservoir in a configuration with said conduit which provides a continuous delivery of a couplant fluid to said raceway forming said means to interpose a couplant fluid between said transducer probe and the wire, said couplant fluid coupling said transducer probe with the wire to accommodate a transmission of said ultrasonic signal and a reflection of said reflected wave.

7. The apparatus according to claim 3, wherein said transducer probe subassembly includes conductor means for connecting said transducer to said data acquisition system.

8. The apparatus according to claim 7, wherein said conductor means include a plurality of conductors.

9. The apparatus according to claim 8, wherein seal means are provided between said upper body and said base where said conductor means exits said base to ensure said reservoir is water tight.

10. The apparatus according to claim 1, wherein said jig assembly includes a roto-pulser assembly comprising a roto-pulser and a roto-pulser wheel, a mounting rotatably means for mounting said wheel, said encoder, and a Bowden cable which connects said roto-pulser wheel to said roto-pulser, said roto-pulser producing a pulse train, whereby said roto-pulser wheel is connected to a roto-pulser by said Bowden cable whereby a single rotation of said roto-pulser wheel produces a predetermined number of pulses which are communicated to said data acquisition system.

11. The apparatus according to claim 10 wherein said roto-pulser wheel is mounted to said jig assembly by a pivoting member which is spring biased to ensure said roto-pulser wheel makes substantially continuous contact with the wire.

12. The apparatus according to claim 1, wherein said data acquisition system includes a central processing unit which processes and stores data, an ultrasonic scope which interfaces with said transducer probe to provide a time analog signal derived from a time of flight comparison between said ultrasonic signal transmitted and said reflected wave received, an analog to digital converter which converts said time analog signal from said ultrasonic scope to a digital signal, a divider circuit which produces a trigger signal which triggers a sample of said digital signal to be processed by said central processing, and a memory means for storing data.

13. The apparatus according to claim 12 wherein said divider circuit includes means producing said trigger signal in response to a predetermined number of pulses produced by said encoder, and said central processing unit includes means providing a reset pulse whereby said divider circuit is reset and begins to count said predetermined number of pulses again.

14. The apparatus according to claim 1, wherein said jig assembly includes a fastening means to mount said jig assembly on a boom which extends from a spring biased swivel base mounted on a mobile means, and a ball and socket configuration, whereby a combination of said spring biased swivel base and said ball and socket configuration ensures a substantially continuous contact of said jig assembly with the wire.

15. The apparatus according to claim 1, wherein said apparatus includes circuitry means for providing proper operation of said data acquisition system and proper communication of said jig assembly and said transducer probe with said data acquisition system.

16. A method for testing wire comprising the steps of:
transmitting an ultrasonic signal into the wire,
monitoring for a reflection of said ultrasonic signal of said transmitting step,
deriving a time differential between said transmitting step and said monitoring step,
producing a time analog signal from said time differential of said deriving step,
converting said time analog signal of said producing step to a digital signal,
generating a pulse train including a plurality of consecutive pulses,
counting a predetermined number of said consecutive pulses, triggering a sample of said digital signal based on said predetermined number of said consecutive pulses of said counting step,
processing said digital signal of said triggering step, and
storing said digital signal of said processing step for future retrieval, whereby
a wire thickness is derived from said time differential between said transmitted ultrasonic signal and a detection of said reflection of said ultrasonic signal and whereby a failure to detect said reflection of said ultrasonic signal indicates wire roll.

17. The method according to claim 16, further comprising the step of:
providing a continuous count of said plurality of consecutive pulses which corresponds to an odometer reading drawing a correlation between a location along the wire and said digital signal of said triggering step,
resetting the count of the counting step after said storing step,
repeating said counting, triggering, processing, storing, and resetting steps to provide a plurality of successive digital signals corresponding to a plurality of successive odometer readings, and wherein said storing step further includes:
storing said plurality of successive digital signals of said process steps of said repeating step and along with each of said corresponding successive odometer readings of said providing step.

18. An apparatus for measuring a wire for thickness and roll, comprising:
a transmitter for transmitting an ultrasonic wave into the wire; and
a receiver for receiving a reflection of the ultrasonic wave transmitted into the wire,
means for measuring a time lapse between the ultrasonic wave being transmitted and the reflection of the ultrasonic wave, said transmitter and said receiver being coupled to said measuring means,
whereby the time lapse is utilized to determine a thickness of the wire and a failure to receive a reflection of the ultrasonic wave being reflected is indicative of a roll in the wire.

* * * * *